(12) United States Patent
Kumabe et al.

(10) Patent No.: US 6,201,070 B1
(45) Date of Patent: Mar. 13, 2001

(54) METHOD FOR ENHANCING THE TOUGHNESS OF CYCLOALIPHATIC EPOXIDE-BASED COATINGS

(75) Inventors: Naofumi Kumabe, Kanagawa (JP); Thomas Andrew Upshaw, Somerset, NJ (US); Robert Francis Eaton, Belle Mead, NJ (US); Bharat Kanaiyalal Patel, Edison, NJ (US); John Kellis Braddock, Three Bridges, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 08/752,541

(22) Filed: Nov. 20, 1996

(51) Int. Cl.$^7$ .................. C07D 301/00; C07D 303/40; C08G 63/91; C08G 59/20

(52) U.S. Cl. ................. 525/327.3; 525/329.7; 525/330.1; 525/449; 525/523; 525/533; 527/311; 527/315; 528/103; 528/110; 536/63; 536/66; 536/84; 536/91; 536/95; 536/96; 536/115; 536/116; 536/119; 536/120

(58) Field of Search ................. 549/561, 547; 528/103, 110; 525/327.3, 329.7, 330.1, 449, 523, 533; 527/311, 315; 536/63, 66, 84, 91, 95, 96, 115, 116, 119, 120; 522/170

(56) References Cited

U.S. PATENT DOCUMENTS

| | | | |
|---|---|---|---|
| 2,794,029 | * | 5/1957 | Phillips et al. ........... 549/547 |
| 2,853,499 | * | 9/1958 | Phillips et al. ........... 549/561 |
| 3,048,601 | | 8/1962 | Frostick et al. .......... 260/348 |
| 3,070,608 | | 12/1962 | Kuester et al. ........... 260/348 |
| 3,454,531 | | 7/1969 | Stewart et al. ........... 260/75 |
| 3,457,238 | | 7/1969 | Carter et al. ............ 260/75 |
| 3,651,098 | * | 3/1972 | Heer et al. ............. 549/561 |
| 3,674,793 | | 7/1972 | Bailey ................. 260/293.54 |
| 4,228,084 | | 10/1980 | Ackerman et al. ......... 260/348.12 |
| 4,812,488 | | 3/1989 | Koleske et al. .......... 522/31 |
| 4,874,798 | | 10/1989 | Koleske et al. .......... 522/31 |
| 4,892,894 | | 1/1990 | Koleske ............... 522/31 |
| 4,977,199 | | 12/1990 | Koleske et al. .......... 522/31 |
| 5,268,489 | | 12/1993 | Koleske et al. .......... 549/215 |

FOREIGN PATENT DOCUMENTS 0 479 166 * 4/1992 (EP) .................. 549/547

969041 10/1961 (GB) .

OTHER PUBLICATIONS

Thomas A. Upshaw et al,. Cycloaliphatic Epoxides, *Research Disclosure*, Jan. 1996 pp. 85–88.

Thomas A. Upshaw et al,. "Intermediates for New Aliphatic Oxlrane Resins", *Research Disclosure*, Feb. 1996 pp. 137–138.

Arnold J. Gordon, et al, *The Chemist's Companion*, John Wiley & Sons, New York, pp. 58,67.

"Cycloaliphatic Epoxide Systems", Cure Chemistry.

Chemical Abstracts, vol. 57, No. 12, Dec. 10, 1962, columns 15035e–15036e, Columbus, Ohio US; L.A. Mukhamedova et al., "The Synthesis and Properties of Dialkyl".

Chemical Abstracts, vol. 60, No. 12, Jun. 8, 1964, columns 14455g–14457a, Columbus, Ohio US; L.A. Mukhamedova et al., "The Synthesis of Some Derivatives of Oxides of Esters of Delta 3–cyclo–hexenecarboxylic Acids" & Neftekhimiya 4(1), 100–5 (1964) *Abstract* .

J. Org. Che, 1985, 50, 912–915 "Chlorohydroxylation of Olefins with Peroxides and Titanium Tetrachloride".

A.E. Batog, O.P. Stepko, and L.P. Nikonova "Kinetics of the Reaction of Alicyclic Monoepoxides with Carboxylic Acids" 971,–974.

A.E. Batog, T.V. Savenko, T.A. Batrak, and R.V. Kucher "Kinetics of the Epoxidation of Cycloalkenes by Aqueous Solutions of Peracetic Acid" 1860–1862.

E. Tucek and H.D. Dinse "Zur Kinetick der Umesterung von Dimethylterephthalat mit Butandiol–1,4"429–433.

Jerald S. Bradshaw et al. " The Synthesis of Macrocylic Polyether–diester Ligands Containing a Long–Chain Alkoxy Substituted Pyridine Sybcyclic Unit" 353–357.

Yohji Nakatsuji et al. "Preparation of Macrocylic Diester and Tetraester Ligands by a Transesterification Process" 19–26.

* cited by examiner

*Primary Examiner*—Frederick Krass
(74) *Attorney, Agent, or Firm*—W. K. Volles

(57) ABSTRACT

Methods are disclosed for enhancing the toughness, e.g., resistance to cracking upon flexation, of coatings made from cycloaliphatic epoxide derivatives wherein the cycloaliphatic epoxide derivative is a cycloaliphatic epoxide ester of a hydroxy-functional compound containing at least one branched, 1,2-alkylene oxide unit. Processes for making the cycloaliphatic epoxide derivatives and coating formulations comprising the cycloaliphatic epoxide derivatives are also disclosed.

11 Claims, No Drawings

METHOD FOR ENHANCING THE TOUGHNESS OF CYCLOALIPHATIC EPOXIDE-BASED COATINGS

FIELD OF THE INVENTION

The present invention generally relates to epoxide-containing compounds and methods for enhancing the toughness of coatings made from such compounds. More specifically, the present invention relates to cycloaliphatic epoxide derivatives of hydroxy-functional compounds having branched, 1,2-alkylene oxide units and the use of such derivatives as coating materials which can have enhanced toughness.

BACKGROUND OF THE INVENTION

Cycloaliphatic epoxides are often used to make cured, i.e., cross-linked, coatings for a variety of articles. When the coatings are applied to certain articles, e.g., food and beverage containers, it is not uncommon for the coatings to be applied to the substrate and cured prior to the fabrication of the article. As a result of the forming operations, the coatings can be subjected to a great deal of mechanical stress upon flexation, i.e., bending, which can cause the coatings to crack. In some cases the coatings are also subjected to retort treatment, i.e., treatment with steam or hot aqueous liquids, for sanitary purposes.

Accordingly, methods for enhancing the toughness, e.g., resistance to cracking upon flexation, of articles coated with cycloaliphatic epoxides are desired. Such methods would be particularly useful in operations where the articles are coated prior to fabrication into the desired shape. In addition, cycloaliphatic epoxide derivatives suitable for use in such methods are also desired. Desirably, the coatings made from such cycloaliphatic epoxide derivatives would also have a sufficient degree of hydrolytic stability to withstand retort treatments.

SUMMARY OF THE INVENTION

By virtue of the present invention, it is now possible to provide cycloaliphatic epoxide-based coatings for articles which have enhanced toughness, e.g., resistance to cracking upon flexation, for example, during fabrication of the article into the desired shape. Quite advantageously, coatings made from the cycloaliphatic epoxide derivatives of the present invention can also have enhanced hydrolytic stability which render the coatings made therefrom suitable for articles which must undergo retort treatment.

In accordance with the present invention, improved cycloaliphatic epoxide derivatives of hydroxy-functional compounds are provided. In the improved derivatives of the present invention, the hydroxy-functional compound has at least one branched 1,2-alkylene oxide unit. As used herein, the term "branched 1,2-alkylene oxide unit" means the moiety illustrated by the following structure:

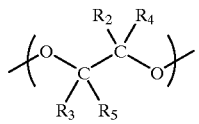

wherein $R_2$–$R_5$ are the same or different and are hydrogen, phenyl or substituted or unsubstituted alkyl or alkene groups each containing 1 to about 10 carbons, provided that at least one $R_2$, $R_3$, $R_4$ or $R_5$ is not hydrogen. Preferably, the branched 1,2-alkylene oxide unit is a propylene oxide unit.

The present invention also provides processes for manufacturing the cycloaliphatic epoxide derivatives by transesterification or epoxidation.

DETAILED DESCRIPTION OF THE INVENTION

The cycloaliphatic epoxide starting materials suitable for use in accordance with the present invention can be any cycloaliphatic epoxides which also have a functional group, e.g., acid, alcohol and preferably ester, which can react with the hydroxyl groups of a hydroxy-functional compound containing one or more branched, 1,2-alkylene oxide units. Typically, the cycloaliphatic epoxides have from about 5 to 7 carbon atoms and preferably 6 carbon atoms in the ring. The cycloaliphatic epoxides can have one or more epoxide groups, and preferably one group, per ring. In addition, the cycloaliphatic epoxides can comprise one or more rings, e.g., up to about 3, as well as other hydrocarbon substituents on the rings and can be saturated or unsaturated.

Preferably, the cycloaliphatic epoxide starting material has the following structure:

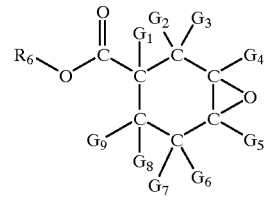

wherein $R_6$ is an organic moiety, preferably hydrogen or a hydrocarbon radical having 1 to about 30 carbon atoms and more preferably a linear or branched alkyl having 1 to about 10 carbon atoms and $G_1$ to $G_9$ are hydrogen, phenyl or substituted or unsubstituted alkyl or alkene having from 1 to about 10 carbon atoms.

Illustrative of the cycloaliphatic epoxides useful as starting materials in the present invention are methyl 3,4-epoxycyclohexane-carboxylate, ethyl 3,4-epoxycyclohexanecarboxylate, propyl 3,4-epoxycyclohexanecarboxylate, isopropyl 3,4-epoxycyclohexanecarboxylate; n-butyl-, i-butyl-, s-butyl-, and t-butyl 3,4-epoxycyclohexanecarboxylate; the various amyl and hexyl 3,4-epoxycyclohexanecarboxylates; methyl 3,4-epoxy-3-methyl-cyclohexanecarboxylate; ethyl 3,4-epoxy-3-methyl-cyclohexanecarboxylate; methyl 3,4-epoxy-4-methyl-cyclohexanecarboxylate; ethyl 3,4-epoxy-4-methyl-cyclohexanecarboxylate; butyl 3,4-epoxy-3-methyl-cyclohexanecarboxylate; butyl 3, 4-epoxy-4-methyl-cyclohexanecarboxylate; methyl 3, 4-epoxy-6-methyl-cyclohexanecarboxylate; ethyl 3,4-epoxy-6-methyl-cyclohexanecarboxylate; butyl 3,4-epoxy-6-methyl-cyclohexanecarboxylate; dialkyl 4,5-epoxycyclo-hexane-1,2-dicarboxylates, as well as mixed dialkyl 4,5-epoxycyclo-hexane-1,2-dicarboxylates, and the like.

The hydroxy-functional compounds suitable for use as starting materials in accordance with the present invention contain at least one branched 1,2-alkylene oxide unit. Typically, the alkylene oxide unit comprises from 3 to about 20 carbon atoms and preferably from about 3 to 6 carbon atoms. More preferably, the branched 1,2-alkylene oxide unit is a propylene oxide unit. The hydroxy-functional compounds can have one or more, preferably 1 to about 10, branched alkylene oxide units per molecule.

In a preferred aspect of the present invention, the hydroxy-functional compounds suitable for use as a starting material have the formula:

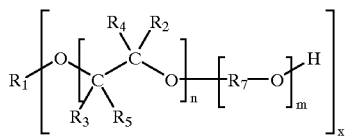

wherein $R_1$ and $R_7$ are organic moieties capable of bonding with oxygen, $R_2$, $R_3$, $R_4$ and $R_5$ are the same or different and are hydrogen, phenyl or substituted or unsubstituted alkyl or alkene groups having from 1 to about 10 carbon atoms, provided that at least one of $R_2$, $R_3$, $R_4$ or $R_5$ is not hydrogen; n has a value of from 1 to about 30, m has a value of from 0 to about 30, and x has a value of from 1 to about 30. When x is greater than 1, then n can be zero in one or more of the additional x-1 groups attached to $R_1$.

In a preferred aspect of the invention, $R_1$ is hydrogen, m is zero, one of $R_2$, $R_3$, $R_4$ or $R_5$ are methyl and the remainder are hydrogen. In another preferred aspect of the invention, $R_1$ and $R_7$ are selected from the group consisting of alcohols, glycols, polyols, hydroxy-functional acrylic polymers and copolymers, hydroxy-functional polysaccharides, hydroxy-functional polyester resins, hydroxy-functional epoxy resins and mixtures thereof. Typically when $R_1$ is not hydrogen, $R_1$ has from 1 to about 50 carbon atoms per molecule.

Apart from the branched, 1,2-alkylene oxide unit(s), the remainder of the hydroxy-functional compound, i.e., $R_1$ and $R_7$ in the immediately preceding above structure, is not critical to the invention and may be any organic moiety, e.g., hydrogen or a hydrocarbon radical containing from 1 to about 30 carbon atoms. However, those skilled in the art will recognize that the remainder of the hydroxy-functional compound, in combination with the branched, 1,2-alkylene oxide unit(s), can also have a significant impact on the properties of the final coating.

In general, suitable hydroxy-functional compounds for use in accordance with the present invention include alcohols, glycols, polyols, and polymeric compounds containing at least one branched, 1,2-alkylene oxide unit. Illustrative of the hydroxyl-containing compounds are propylene glycol, di-, tri-, and tetra-propylene glycol as well as other poly(propylene glycols); trifunctional polypropylene oxide)s including ethylene oxide-capped and F-caprolactone-capped propylene oxide polyols that contain up to above 25% by weight ethylene oxide or propylene oxide; random, block, and graft ethylene oxide/propylene oxide copolymers; propoxylated polyester polyols including propoxylated hexanediol adipates, butylene adipates, ethylene adipates, butylene succinates, etc; propoxylated polycarbonate polyols; hydroxypropyl cellulose; hydroxyalkyl acrylates such as hydroxyethyl acrylate, hydroxypropyl acrylate after reaction with various amounts of propylene oxide, and optionally ethylene oxide or caprolactone; or caprolactone acrylates after reaction with various amounts of propylene oxide and optionally ethylene oxide; and the like.

When the hydroxy-functional compound is a polymer, e.g., polypropylene glycol), the polymer preferably has a number average molecular weight of from about 100 to 3000 grams per gram-mole. Methods for determining number average molecular weight are known to those skilled in the art. One such method is size exclusion chromatography ("SEC").

Some specific examples of hydroxy-functional compounds suitable for use in accordance with the present invention include, but are not limited to propoxylated 2,2-dimethyl-1,3-propanediol, propoxylated 2-methyl-1,3-propanediol, propoxylated 2-butyl-2-ethyl-1,3-propanediol, propoxylated 2,2-diethyl-1,3-propanediol, propoxylated 2,2-bis(hydroxymethyl)-1-butanol, propoxylated pentaerythritol, propoxylated dipentaerythritol, propoxylated tripentaerythritol, propoxylated sorbitol, propoxylated glycerol, propylene glycol, branched 1,2-butylene glycol, dipropylene glycol, tripropylene glycol, tetrapropylene glycol, polybutylene oxide, polypropylene oxide, propoxylated hydroxy-functional acrylic polymers and copolymers, propoxylated 2-hydroxyethyl methacrylate, propoxylated 2-hydroxyethyl acrylate, 2-hydroxypropyl methacrylate, 2-hydroxypropyl acrylate, 2-hydroxybutyl methacrylate, 2-hydroxybutyl acrylate, hydroxypropyl cellulose, propoxylated bis-phenol A, propoxylated bis-phenol A epoxy resins, branched 1,2-alkylene oxide unit-containing hydroxy-functional polyester resins, propoxylated fatty alcohols, propoxylated dimer acid alcohols, hydroxy-functional copolymers of propylene glycol or polypropylene glycol with e-caprolactone, and hydroxy-functional copolymers of propylene glycol or polypropylene glycol with adipic acid and optionally other acids and alcohols.

Hydroxy-functional compounds such as described above are commercially available. Further details concerning such hydroxy-functional compounds are known to those skilled in the art.

Typically the cycloaliphatic epoxide derivatives of the present invention will comprise the reaction products of from about 10 to 95, preferably from about 20 to 90 and more preferably from about 40 to 90 weight percent of the cycloaliphatic epoxide and typically from about 5 to 90, preferably from about 10 to 80 and more preferably from about 10 to 60 parts by weight percent of the hydroxy-functional compound based upon the total weight of the cycloaliphatic epoxide derivative (cycloaliphatic epoxide plus hydroxy-functional compound).

In a preferred aspect of the present invention, the cycloaliphatic epoxide derivative has the formula:

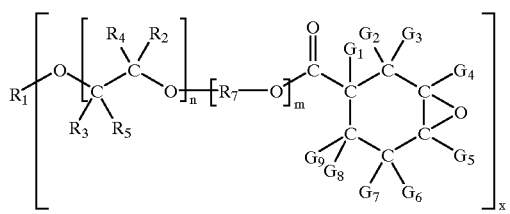

wherein $R_1$ and $R_7$ are organic moieties capable of bonding with oxygen, $R_2$, $R_3$, $R_4$ and $R_5$ are the same or different and are hydrogen, phenyl or substituted or unsubstituted alkyl or alkene groups, having from 1 to about 10 carbon atoms, provided that at least one of $R_2$, $R_3$, $R_4$ or $R_5$ is not hydrogen; $G_1$ to $G_9$ are the same or different and are hydrogen, phenyl or substituted or unsubstituted alkyl or alkene groups having from 1 to about 10 carbon atoms; n has a value of from 1 to about 30, m has a value of from 0 to about 30, and x has a value of from 1 to about 30. When x is greater than 1, then n can be zero in one or more of the additional x-1 groups attached to $R_1$.

In a preferred aspect of the invention, $R_1$ is hydrogen, m is zero, one of $R_2$, $R_3$, $R_4$ or $R_5$ are methyl and the remainder are hydrogen. Alternatively, $R_1$ and R7 can be selected from the group consisting of alcohols, glycols, polyols, hydroxy-functional acrylic polymers and copolymers, hydroxy-functional polysaccharides, hydroxy-functional polyester resins, hydroxy-functional epoxy resins and mixtures thereof. Typically when $R_1$ is not hydrogen, $R_1$ has from 1 to about 50 carbon atoms per molecule.

Especially preferred cycloaliphatic epoxide derivatives of the present invention are selected from the group consisting of: the mono(3,4-epoxycyclohexanecarboxylic ester) of propylene glycol; the bis(3,4-epoxycyclohexanecarboxylic ester) of propylene glycol; the mono(3,4-epoxycyclohexanecarboxylic ester) of dipropylene glycol; the bis(3,4-epoxycyclohexanecarboxylic ester) of dipropylene glycol; the mono(3,4-epoxycyclohexanecarboxylic ester) of tripropylene glycol; the bis(3,4-epoxycyclohexanecarboxylic ester) of tripropylene glycol; the mono(3,4-epoxycyclohexanecarboxylic ester) of polypropylene glycol; the bis(3,4-epoxycyclohexanecarboxylic ester) of polypropylene glycol the mono(3,4-epoxycyclohexanecarboxylic ester) of poly(1,2-butylene glycol); the bis(3,4-epoxycyclohexanecarboxylic ester) of poly(1,2-butylene glycol); the mono(3,4-epoxycyclohexanecarboxylic ester) of propoxylated Bisphenol-A; the bis(3,4-epoxycyclohexanecarboxylic ester) of propoxylated Bisphenol-A; the mono(3,4-epoxycyclohexanecarboxylic ester) of propoxylated trimethylolpropane; the bis(3,4-epoxycyclohexanecarboxylic ester) of propoxylated trimethylolpropane; the tris(3,4-epoxycyclohexanecarboxylic ester) of propoxylated trimethylolpropane; the momo(3,4-epoxycyclohexanecarboxylic ester) of propoxylated glycerol; the bis(3,4-epoxycyclohexanecarboxylic ester) of propoxylated glycerol; the tris (3,4 epoxycyclohexanecarboxylic ester) of propoxylated glycerol; and mixtures thereof.

The particular process used for manufacturing the cycloaliphatic epoxide derivatives of the present invention is not critical. Preferred processes include transesterification such as disclosed in European Patent Application Publication No. 0 479 166 A1 published Apr. 8, 1992, and epoxidation such as disclosed, for example in U.S. Pat. No. 5,268,489 issued Dec. 7, 1993.

When the cycloaliphatic epoxide derivatives of the present invention are prepared by transesterification, a cycloaliphatic epoxide ester, e.g., an alkyl 3,4 epoxycyclohexanecarboxylate, is combined with a hydroxy-functional compound and an optional catalyst. The mixture is then stirred in bulk or in dilution with an optional solvent and heated for an amount of time effective to react the desired amount of the cycloaliphatic epoxide ester onto the hydroxy-functional compound. In general, it is advantageous to remove any by-products, like alcohols, by distillation or sparging with a dry gas such as argon or nitrogen. A solvent which forms an azeotrope with the by-product can optionally be used to facilitate its removal. The reaction can be carried to completion or only partially completed to provide a mixture of epoxy-functional compounds.

The starting mole ratio of epoxide groups to hydroxyl groups can be any desired ratio. If it is desired to obtain a substantially complete conversion to a product with a high amount of epoxy substituents, the starting epoxide to hydroxyl mole ratio should be greater than 1, preferably about 1 to 3 and most preferably about 1.1 to 2. When an excess of the cycloaliphatic epoxide starting material is used, the excess, if any, can be easily removed upon completion of the reaction by distillation under vacuum conditions. Alternatively, if a product with a low residual monomer content is desired, it is advantageous to utilize a starting epoxide to hydroxyl mole ratio of less than 1, preferably about 0.9:1 and more preferably about 0.95:1. If a product is desired with only partial epoxide substitution and containing some remaining hydroxy-functionality, then it is advantageous to use a starting epoxide to hydroxyl mole ratio of significantly less than 1, preferably about 0.2 to 0.9 and more preferably about 0.4 to 0.85. In all cases, but particularly in cases where in the epoxide to hydroxyl mole ratio is significantly less than 1, care must be taken to avoid excessive temperatures and reaction times which can lead to oligomerization of the product with a corresponding increase in viscosity and reduction in functionality.

The transesterification reaction can be carried out at temperatures effective to conduct the transesterification, e.g., about 50° C. to 250° C., and preferably at temperatures of about 70° C. to 200° C. The time for completion of the transesterification reaction will typically range from about 10 minutes to 40 or more hours depending on the temperature employed and the particular ingredients involved. The preferred time of reaction is from about one to eight hours. The transesterification can be carried out under atmospheric pressure, subatmospheric pressure, or superatmospheric pressure; however, it is preferred that the reaction be carried out at pressures of about 0.001 atmosphere to about 1.5 atmosphere. The particular process parameters employed will depend on the particular ingredients used, as well as the batch size, the details of which are known to those skilled in the art.

Illustrative of the catalysts useful for the transesterification reaction are salts of weak acids such as, for example, sodium bicarbonate, potassium bicarbonate, potassium thiocyanate, barium thiocyanate, calcium thiocyanate, cesium thiocyanate, cobalt thiocyanate, lead thiocyanate, lithium thiocyanate, sodium thiocyanate, zinc thiocyanate, other salts of weak acids such as sodium acetate, lithium acetate, potassium acetate, cesium acetate, calcium acetate, zinc acetate, sodium propionate, potassium butyrate, calcium isobutyrate, zinc 2-ethylhexanoate, and other metal salts of acetic acid, carbonic acid and carboxylic acids, alkali metal alkoxides such as sodium methoxide, potassium methoxide, lithium methoxide, zinc methoxide, calcium methoxide, cesium methoxide, potassium t-butoxide, potassium n-butoxide, sodium i-propoxide, lithium ethoxide, potassium cyanide, sodium cyanide, metal oxalates, calcium hydride, cesium fluoride, and the like. In addition, mixtures of the catalysts can be used when desired. The catalysts are typically used in amounts of from about 0.0005 mole percent to 1 mole percent, preferably from about 0.001 mole percent to 0.5 mole percent, and most preferably from about 0.001 mole percent to 0.1 mole percent based on the total moles of hydroxyl groups in the starting hydroxy-functional compound. The catalyst may be added to the reaction mass all at one time, in discrete portions that may be of the same or different size, or in a continuous uniform or non-uniform manner over the entire reaction time period or over a portion of the reaction time period.

For example, with a catalyst like sodium acetate, using about 30 wt % heptane solvent relative to the total weight of reactants, a suitable reaction temperature is usually from about 100 to 150° C. and preferably 110 to 130° C. For a more reactive catalyst like alcoholic sodium methoxide, a suitable reaction temperature can be much lower, usually −40 to 100° C., preferably −10 to 80° C.

The optional solvent can be left in the reaction mixture or can be removed at the end of the reaction by distillation or by other techniques known to those skilled in the art.

The presence of water is generally not advantageous in the reaction, and pre-drying of the starting materials can optionally be carried out by heating the combined reaction components with a water-azeotroping solvent at the solvent's boiling temperature to facilitate water removal before adding the catalyst. Alternatively or in addition, drying can be accomplished by sparging the heated reaction mixture with a dry gas, treating with molecular sieves or by any other methods known to those skilled in the art.

Further details concerning transesterification are known to those skilled in the art. Note, for example, European Patent Publication No. 0 479 166 A1.

The cycloaliphatic epoxide derivatives of the present invention can also be prepared by epoxidation according to methods known in the art. Note for example, N. Kumabe, T. A. Upshaw, Research Disclosure, 85–88, January 1996, and 137–138 February 1996.

In the epoxidation reaction, epoxidizing agents of various types can be used. These agents can be formed in situ from hydrogen peroxide and an organic acid such as acetic acid and optionally a catalyst such as sulfuric acid, from ozone and an aldehyde such as acetaldehyde, can be pre-formed and used as a peracid, or can be in the form of a dioxirane such as dimethyldioxirane, and the like. Illustrative of the peracids that can be used in carrying out epoxidations are perbenzoic acid, peracetic acid, perpropionic acid, percaproic acid, permonochloroacetic acid, meta-chloroperoxybenzoic acid, perbutyric acid, perlactic acid, permonosuccinic acid, t-butylperbenzoic acid, and the like. When used, the peracids are usually dissolved in a solvent such as ethyl acetate to minimize explosive and other hazards.

In this reaction, an unsaturated, cycloaliphatic compound, e.g., a 3-cyclohexanecarboxylic acid ester of a di- or multi hydroxy-functional compound, is reacted with the epoxidizing agent at temperatures of less than about 5° C. to 90 C., preferably at temperatures of about 10° C. to 80 C., and most preferably at temperatures of about 20 to 70° C. The time required for reaction will vary depending upon the particular reactants charged and the temperature, the details of which are well known to those skilled in the art of epoxidation chemistry. Typical reaction pressures are from about 0.1 atm to 10 atm. In general, the peracid solution is carefully and very slowly added to the reactor containing the starting materials, in either a neat form or preferably dissolved in a suitable inert solvent such as ethyl acetate, which is held at a relatively constant reaction temperature. The reaction can be optionally carried out in a series of reaction vessels with different set temperatures and configurations. The rate of peracid addition should be such that a desired maximum temperature is not exceeded. The exothermic oxidation reaction that takes place is controlled by cooling the reaction mass to the desired reaction temperature. The peracid addition rate is decreased or stopped if necessary to maintain temperature control. A method of quenching the reaction is usually made available and maintained as, for example, in the laboratory an ice/water bath is available. The reaction product is then optionally washed one or more times with water to remove by-product acid, such as acetic acid when peracetic acid is used, and oxidizing agent. The product is isolated by vacuum stripping of the organic acid that is formed and the solvent that had been used to dissolve the starting materials. Optionally, the product may be washed one or more times with water. If desired, the product may be redissolved and reisolated by vacuum stripping using conventional techniques, distillation, or other recovery methods.

Further details concerning epoxidation are known to those skilled in the art.

Quite surprisingly, in accordance with the present invention, it has been found that the use of the branched, 1,2-alkylene oxide units, e.g., propylene oxide units, in the hydroxy-functional compounds can enhance the efficiency of the processes for making the derivatives of the present invention according to the transesterification route. This finding is surprising since those skilled in the art would expect a hydroxyl group attached to an unbranched, e.g., ethylene oxide, group, to be more reactive than those attached to a branched group, due to steric hindrance near the reaction site. In the present invention, it has been found that propylene oxide-type hydroxyl groups can undergo the transesterification reaction more rapidly, proceed to a higher extent of reaction, and give products containing less impurities from decomposition than, e.g., ethylene glycol-type hydroxyl groups.

The cycloaliphatic epoxide derivatives of the present invention can be used for a broad variety of end uses including, for example, coatings for food and beverage containers, automotive coatings, general metal coatings, decorative coatings, electronics coatings including, for example, solder masks, photoresists, and conformal coatings, protective coatings for compact and optical discs, and the like, as well as inks, molded objects, sealants and adhesives used in the automotive, home and electronic industries.

The coatings can be applied by various techniques, illustrative of which are spray coating, roll coating, dip coating, electrodeposition, brush, and the like. The coatings can be cured by a variety of techniques, including radiation, thermal, air drying, and the like, depending on the particular system being formulated.

The cycloaliphatic epoxide derivatives of the present invention can be advantageously used in a method to enhance the toughness, e.g., resistance to cracking upon flexation, of a coating on an article. As a result, coatings made from the cycloaliphatic epoxide derivatives of the present invention can be particularly useful when applied to substrates prior to forming the substrates into the desired shapes to form the article. This formation technique is common in the manufacture of beer and beverage containers, food containers, and other rigid containers. In addition, coatings made from the cycloaliphatic epoxide derivatives of the present invention can have a high degree of hydrolytic stability which renders them suitable for applications which undergo retort treatment, e.g., to sanitize the articles.

In producing coatings curable with actinic radiation, and preferably ultraviolet light, the cycloaliphatic epoxide derivatives are often combined with other cycloaliphatic epoxides, Novolac epoxides, and the like; vinyl ethers; acrylates and methacrylates; polyols; onium salt, diazonium salt or other cationic photoinitiators; and, if desired, surfactants; oils; fillers and other additives known to those skilled in the art. The formulated coatings may contain inert solvents or reactive diluents for the purpose of decreasing viscosity and improving application characteristics or inert polymers, fumed silicas, and the like, to thicken the formulated coating and make it useful in screen printing or other operations. The coatings are typically cured by exposure to ultraviolet light radiation from a medium pressure mercury vapor lamp with radiation between about 220 and 400 nanometers. Further details concerning the selection and amounts of such additional materials are known to those skilled in the art. See, for example, U.S. Pat. No. 5,268,489. The photocurable compositions typically contain, exclusive of photoinitiator, from about 25 to 100 percent of the cycloaliphatic epoxide derivatives, from 0 to about 60 percent of other hydroxyl-containing compounds, from 0 to about 75 percent of other cycloaliphatic or other epoxide, from 0 to about 60 percent vinyl ether, and from 0 to about 60 percent acrylate.

The thermally-curable compositions can contain suitable catalysts such as, for example, sulfuric acid, hydrochloric acid, p-toluene sulfonic acid, methyl sulfonic acid, phosphoric acid and alkyl derivatives of phosphoric acid, maleic acid, trimellitic acid, triflic acid, salts of triflic acid such as the diethylammonium salt of triflic acid, the ammonium salt of triflic acid, the stannous salt of triflic acid, stannous octanoate, uranyl nitrate, zinc octanoate, and the like, including mixtures of these catalysts. The thermally-curable compositions typically contain, exclusive of catalyst, from about 25 to 100 percent of the cycloaliphatic epoxide derivative, from 0 to about 60 percent of other hydroxyl-containing compounds, and from 0 to about 75 percent of other cycloaliphatic or other epoxides. The thermally-curable compositions may also contain other ingredients such as one or more surfactants, flow and leveling agents, fumed silicas, silicone oils and other slip agents, and other ingredients suitable for coatings known to those skilled in the art. Thermal curing is typically conducted by heating at a suitable temperature generally from about 50° C. to about 275° C., preferably from about 90° C. to about 200° C., for a period of time sufficient to obtain a dry film. Generally this time will range from about one minute to about two hours.

A convenient way to characterize the toughness of coatings is by measuring the wedge bend performance both before and after retort processing. The Wedge Bend Test and Wedge Bend Value are further described hereinafter in the Examples. The ratio of the Wedge Bend Value after retort processing to the Wedge Bend Value prior to retort processing (referred to hereinafter as "Wedge Bend Ratio") provides an indication of the hydrolytic stability of the coating. The closer the Wedge Bend Ratio is to 1 the more hydrolytically stable the coating is. The Wedge Bend Values of the coatings made in accordance with the present invention are typically less than 50 millimeters, preferably less than about 40 millimeters and more preferably less than about 30 millimeters. The Wedge Bend Ratios of the coatings made in accordance with the present invention are typically less than about 2, preferably less than about 1.8 and more preferably less than about 1.5.

EXAMPLES

The following examples present illustrative aspects of this invention and are not intended to limit its scope. All of the parts, percentages and proportions referred to are by weight unless otherwise indicated. All of the ingredients used in the Examples are readily commercially available unless otherwise indicated. The following terms used in the examples have the following meanings:

| DESIGNATION | DESCRIPTION |
| --- | --- |
| Cyracure ® UVI-6990 | Hexafluoroantimonate sulfonium salt, available as CYRACURE ® UVI-6990 from Union Carbide Corporation, Danbury, CT |
| TONE ®-0301 | Trihydroxyl functional ε-caprolactone polyol with an average hydroxyl number of 560 and an average hydroxyl equivalent weight of 100, available as TONE ®-0301 from Union Carbide Corporation, Danbury, CT |
| TONE ®-0305 | Trihydroxyl functional ε-caprolactone polyol with an average hydroxyl number of 312 and an average hydroxyl equivalent weight of 180, available as TONE ®-0305 from Union Carbide Corporation, Danbury, CT |
| Dimer Diol | A dimerized fatty acid alcohol, available as Pripol 2033 from Unichema North America, Chicago, IL |
| DC-57 | A silicone surfactant available as "57 Additive" from Dow-Corning Co., Midland, MI |
| UVR-6128 | 3,4-Epoxycyclohexylmethyl diester of adipic acid, available as CYRACURE ® UVR-6128 from Union Carbide Corporation, Danbury, CT |
| UVR-6110 | 3,4-Epoxycyclohexylmethyl 3,4-epoxycryclohexanecarboxylate, available as CYRACURE ® UVR-6110 from Union Carbide Corporation, Danbury, CT |
| Silwet L-7604 | A silicone surfactant available as Silwet ® L-7604 from OSi Specialties, Endicott, NY |
| Photonol 7143 Photonol 7158 | Polyether polyols available as Photonol 7143 and Photonol 7158 from Henkel Corp., Ambler, PA |

Measurements and test procedures used in the examples are as follows:

MEK Resistance Solvent Resistance (Double Methyl Ethyl Ketone Rubs)

A measure of the resistance of the cured film to attack by methyl ethyl ketone (MEK) in which a film coating surface was rubbed with an MEK-soaked cotton swab back and forth with hand pressure until the coating was penetrated to the substrate. A rub back and forth over the film coating surface under moderate pressure with the MEK-soaked cotton swab was designated as one "double MEK rub".

Pencil Hardness

Each coating formulation to be tested was applied and cured on a substrate consisting of a tin-free steel panel (can-end tin-free steel from Weirton Steel Corp., Weirton, W.Va.). Pencil leads of increasing hardness values were forced against the film coating surface in a precisely defined manner as described in ASTM D-3363-74 until one pencil lead cut through the surface of the film coating. The surface hardness was considered as the hardest pencil grade which just failed to cut or mar the film coating surface. The pencil leads in order of softest to hardest were reported as follows: 6B, 5B, 4B, 3B, 2B, B, HB, F, H, 2H, 3H, 4H, 5H, 6H, 7H, 8H and 9H.

Aluminum Pencil Hardness

The same test as Pencil Hardness (above), except that the coating formulations were applied and tested on an aluminum panel substrate (Wrought Aluminum Alloy #5182 from Reynolds Metals Co., Richmond, Va.).

Wedge Bend Test

Before testing, all panels were UV-cured and then post-baked at 400° F. for 10 minutes to complete the cure. The wedge bend test was carried out according to ASTM Method D-3281-84, except that the crack was visually enhanced before measuring its length by treating the panel with a 70:20:10 (by volume) mixture of water, copper (II) sulfate and concentrated aqueous hydrochloric acid. This copper sulfate treatment was only applied to panels measured before retort. Wedge bending was performed before retort. Crack length was measured on representative panels before and after retort treatment. The crack length in millimeters is the Wedge Bend Value.

Retort Treatment

Retort treatment consisted of placing the panels in a rack in an autoclave for 1 hour under conditions where deionized water placed below the panels was converted into steam (250° F., 15 psig). After treatment, the panels were dried off and allowed to cool for about 10 minutes, then the crack length was measured according to the wedge bend method above.

Example 1

Preparation of Tripropylene glycol 3,4-epoxycyclohexanecarboxylate adduct

Methyl 3,4-epoxycyclohexanecarboxylate (50 g), and tripropylene glycol (33.8 g) in 60 milliliters ("mL") of heptane were heated in a flask equipped with a 120-mL insulated Vigreaux column, Dean-Stark trap, drying tube and magnetic stirrer. The Dean-Stark trap was pre-filled with heptane. After refluxing the heptane for 60 minutes to azeotropically remove any water moisture, 0.0340 g of anhydrous sodium acetate (406 ppm by weight based on undiluted starting materials) was added as a transesterification catalyst. Methanol/heptane azeotrope was collected in the Dean-Stark trap and heating was continued for 405 minutes. The reaction temperature gradually increased from 102 to 113° C. during the course of the reaction, and the lower (methanol-rich) layer had a volume of 20.2 mL. Heating was continued and a nitrogen sparge was used to help remove any remaining heptane solvent by distillation. The product was allowed to cool to room temperature. The product consisted of 86 wt % of the mono and diepoxide adducts of tripropylene glycol, 0.8 wt % residual monoepoxide, and 14 wt % higher oligomers by uncorrected size-exclusion chromatography using THF solvent and a refractive index detector. Purity by gas chromatography was 88%. The viscosity of the product was 380 centipoise (cP) and the epoxy equivalent weight (titration) was 245 (theoretical 230). The product resin was formulated into a photo-crosslinkable material without further purification.

Examples 2 to 9 and Comparative Examples 1 to 13

Preparation of Various 3,4-epoxycyclohexane adducts

The cycloaliphatic epoxide derivatives set forth in Table 1 below were prepared following the procedure set forth in Example 1. The properties of the products are listed in Table 1. The reaction times and temperatures were varied in the Examples from about 200 to 1500 minutes and 100 to 150° C., respectively. The amount of heptane used as co-solvent to help remove the methanol by-product was between 17 and 42% by weight of the total reactants charged.

TABLE 1

| | | Product Characterization | | | | Epoxy | | |
|---|---|---|---|---|---|---|---|---|
| Example No. | Hydroxy Functional Compound | Mono and Di Epoxide Adduct SEC (wt. %)[1] | GC Residual Mono Epoxide GC (wt. %)[2] | Higher Oligomers SEC (wt %)[1] | GC Purity (wt. %)[2] | Equivalent Weight Actual | Theoretical | Viscosity (cP) |
| 2 | dipropylene glycol | 83 | 0.3 | 17 | 91 | 211 | 198 | 510 |
| Comparative 1 | diethylene glycol | 63 | 3.5 | 37 | 63 | 208 | 183 | 650 |
| 3 | propylene glycol | 76 | 0.6 | 24 | 84 | 182 | 195 | 526 |
| Comparative 2 | ethylene glycol | 63 | 0.5 | 37 | 82 | 174 | 158 | 1100 |
| 4 | polypropylene glycol ($M_n$ = 425) | 97 | 0.7 | 3 | — | 375 | 358 | 295 |
| 5 | polypropylene glycol ($M_n$ = 100) | 94 | 0.4 | 6 | — | 728 | 675 | 339 |
| 6 | Bisphenol A propoxylate ($M_n$ = 645) | 99 | 1.0 | 1 | — | 491 | 480 | 8840 |
| 7 | Bisphenol A propoxylate ($M_n$ = 344) | 89 | 1.7 | 11 | — | 332 | 317 | _[3] |
| Comparative 3 | Bisphenol A ethoxylate ($M_n$ = 404) | 66 | 1.4 | 34 | — | 404 | 346 | _[3] |
| Comparative 4 | Bisphenol A[3] | | | | | | | |
| 8 | Propoxylate trimethylol propane | 94[4] | 0.4 | 6 | — | 246 | 234 | 6780 |
| Comparative 5 | Ethoxylated trimethylol propane ($M_n$ = 270) | 20[2] | 1.3 | 80 | — | 362 | 273 | _[5] |
| Comparative 6 | Ethoxylated trimethylol propane ($M_n$ = 750) | 66[2] | 1.4 | 34 | — | 462 | 400 | 1200 |
| Comparative 7 | TONE ® 0301 polycaprolactone triol | — | — | — | — | 237 | 224 | 5900 |
| Comparative 8 | Trimethylol propane | 41[2] | 1.7 | 59 | — | 209 | 173 | _[3] |
| 9 | Poly (1,2 butylene glycol) | 98 | 0.4 | 2 | — | 436 | 412 | 343 |
| Comparative 9 | Dimer Diol | 90 | — | 9.5 | — | 453 | 437 | 860 |
| Comparative 10 | 1,5-pentanediol | 86 | 0.2 | 14 | 85 | 190 | 181 | 265 |

TABLE 1-continued

| | | Product Characterization | | | | Epoxy | | |
| --- | --- | --- | --- | --- | --- | --- | --- | --- |
| | Hydroxy Functional | Mono and Di Epoxide Adduct | GC Residual Mono Epoxide | Higher Oligomers | GC Purity | Equivalent Weight | | Viscosity |
| Example No. | Compound | SEC (wt. %)[1] | GC (wt. %)[2] | SEC (wt %)[1] | (wt. %)[2] | Actual | Theoretical | (cP) |
| Comparative 11 | 1,8-octanediol | 86 | 0.1 | 14 | 87 | 216 | 204 | 211 |
| Comparative 12 | 1,6-hexanediol | 88 | 0.6 | 12 | 86 | 204 | 189 | 215 |
| Comparative 13 | 1,4-butanediol | 80 | 0.2 | 20 | 85 | 183 | 174 | 305 |

[1]As measured by Size-exclusion Chromatography
[2]As measured by Gas Chromatography
[3]Product was solid and insoluble.
[4]Product also contained triepoxide adduct.
[5]Viscosity too high to measure.

Example 10

Preparation of Tripropylene glycol, 3,4-epoxycyclohexane-carboxylate adduct via peracetic acid epoxidation A reaction mixture composed of 3-cyclohexenecarboxylic acid (630.8 g), tripropylene glycol (384.5 g), and methanesulfonic acid (10.15 g) in 305 g of toluene was heated in a flask equipped with a 120-mm insulated Vigreaux column, Dean-Stark trap, drying tube and magnetic stirrer. The Dean-Stark trap was pre-filled with toluene. After refluxing the toluene (reaction vessel temperature 150° C.) for 8.5 hours to azeotropically remove the water of reaction, the lower (aqueous) layer in the Dean-Stark trap had a volume of 81 mL. The mixture was allowed to cool down and an additional 126 grams of 3-cyclohexenecarboxylic acid, 100 mL of toluene and 1.0 gram of methanesulfonic acid were added. Heating was resumed for 20 hours, but only 2 additional mL of aqueous layer was collected. The reaction mixture was allowed to cool and was washed with 1500 mL of saturated aqueous $NaHCO_3$, and dried over 100 g of anhydrous $Na_2SO_4$.

The dried mixture was passed through a Pope® wiped-film evaporator (WFE) (available from Pope Scientific, InC, Menomenee Falls, Wis.) equipped with a cooling finger and overhead lights condenser, at 120° C. and 110 mmHg, yielding 368 grams of distillate and 1011 grams of residue product. Feed time was 75 minutes. The residue product was passed through the WFE again at 150° C. and 5 mmHg over 90 minutes, and yielded 808 grams of residue product. A third WFE pass of the residue under the same conditions afforded 790 grams of residue product. A fourth WFE pass at 180° C. and 0.1–0.15 mmHg gave 519 grams of residue product. A fifth WFE pass under the same conditions gave 217.6 grams of the distilled product, tripropylene glycol bis(3-cyclohexenecarboxylate) as a yellow liquid. The intermediate tripropylene glycol bis(3-cyclohexenecarboxylate) (214 g) was charged to a flask equipped with a reflux condenser, addition funnel and mechanical stirrer, along with 200 grams of ethyl acetate. A 25 wt % solution of peracetic acid in ethyl acetate (334.6 grams) was charged to the addition funnel and added to the reaction vessel over the course of 20 minutes, adjusting the vacuum on the system to maintain a reaction temperature between 38 and 41° C. by keeping the ethyl acetate at reflux.

The mixture was stirred overnight at ambient pressure, and passed through a Pope® wiped-film evaporator (WFE) at 120° C. and 120 mmHg. Feed time was 75 minutes. The residue product (263 g) was neutralized with a mixture of 260 g saturated aqueous $NaHCO_3$ solution and 200 g of distilled water. The organic phase was washed with 800 g distilled water, separated and diluted with 350 grams of chloroform and 500 grams of water. The organic phase was separated, dried repeatedly with anhydrous $Na_2SO_4$, filtered, and passed through silica gel to filter out a hazy precipitate.

The clear yellow mixture was passed through the Pope® WFE at 120° C. and atmospheric pressure to remove the solvent. The residue product (209 g) was passed through the WFE again at 200° C. and 0.1 mmHg over the course of an hour, yielding 80 grams of distilled product, tripropylene glycol bis(3,4-epoxycyclohexanecarboxylate). The product consisted of 82 wt % of the diepoxide adduct of tripropylene glycol and 6 wt % of the monoepoxide adduct of tripropylene glycol by GC, and 0.4 wt % higher oligomers by uncorrected size-exclusion chromatography using THF solvent and a refractive index detector. The viscosity of the product was 460 cP, and the epoxy equivalent weight (titration) was 234 (theoretical 220). The product resin was formulated into a photo-crosslinkable material without further purification.

Example 11

Evaluation of Ester Epoxides in UV Coating Applications

Various epoxide based coatings were evaluated in can-end varnish-type testing. The formulation was as follows:

| Component | Wt. % |
| --- | --- |
| Cycloaliphatic Epoxide | 95.5 |
| Cyracure ® UVI-6990 | 4.0 |
| DC-57 | 0.5 |

The formulation containing epoxide of Example 7 had 15% MEK added to reduce viscosity to a usable level and was applied onto tin-free steel and can-end aluminum panels with a #3 wirewound drawdown bar. All other epoxides were applied with a #2.5 wirewound drawdown bar to give approximately 0.15–0.17 mils cured film thickness. All coatings were cured with 150 $mJ/cm^2$ UV dose and were baked for 10 minutes at 400 F. to simulate can end production. Cure rate was run on aluminum coated paper with one 200 W/in Linde lamp at 35% RH. Wedge bend performance was determined by measuring the crack length (mm) after wedge bending the coated steel. (see wedge bend and retort procedures described above).

The wedge bend results are as follows:

TABLE 2

Wedge Bend Values Before and After Retort

| Epoxide of Example | Avg. Wedge Bend, mm (2 trials) | Avg. Retort Wedge Bend, mm (2 trials) | Wedge Bend Ratio |
|---|---|---|---|
| UVR-6110 | 63 | 66 | 1.0 |
| UVR-6128 | 20 | 40 | 2.0 |
| Ex. 1 | 16 | 27 | 1.7 |
| Ex. 2 | 22 | 27 | 1.2 |
| Comp. Ex. 1 | 30 | 95 | 3.2 |
| Ex. 3 | 52 | 61 | 1.2 |
| Comp. Ex. 2 | 49 | 65 | 1.3 |
| Ex. 6 | 1 | 2 | — |
| Ex. 7 | 100+ | 100+ | — |
| Ex. 8 | 26 | 37 | 1.4 |
| Comp. Ex. 7 | 17 | 48 | 2.8 |
| Comp. Ex. 10 | 22 | 42 | 1.9 |
| Comp. Ex. 11 | 15 | 40 | 2.7 |
| Comp. Ex. 12 | 17 | 40 | 2.4 |
| Comp. Ex. 13 | 23 | 44 | 1.9 |

The adduct of Example 7, 344 $M_n$ propoxylated bisphenol A, exhibited very bad blistering after retort processing. The coating appeared to be solubilized by the steam during retort testing.

The adhesion, pencil hardness, MEK resistance, and cure rate results are as follows:

TABLE 3

Hardness and Cure

| Epoxide of Example | Pencil Hardness | Aluminum Pencil Hardness | MEK Resistance (double rubs) | Surface Cure Rate, fpm[1] |
|---|---|---|---|---|
| UVR-6110 | 5H | 7H | 200+ | 575 |
| UVR-6128 | 3H | 3H | 12 | 225 |
| Ex. 1 | 2H | 2H | 4 | 90 |
| Ex. 2 | 3H | 2H | 7 | 175 |
| Comp. Ex. 1 | 3H | 2H | 20 | 210 |
| Ex. 3 | 2H | 2H | 40 | 270[3] |
| Comp. Ex. 2 | F | 3H | 190 | 510 |
| Ex. 6 | 6B | 6B | 2 | <20[3] |
| Ex. 7 | 2B | 2B | 1 | 460[3] |
| Ex. 8 | 3H | — | 38 | NA |
| Comp. Ex. 7 | 2H | 3H | 38 | 290 |
| Comp. Ex. 10 | F | 2H | 24 | 280 |
| Comp. Ex. 11 | 2H | 3H | 6 | 160[2] |
| Comp. Ex. 12 | 2H | 3H | 20 | 235 |
| Comp. Ex. 13 | H | 3H | 120 | 350 |

[1]35% relative humidity (RH) unless otherwise noted.
[2]38% RH
[3]42% RH

Cyracure® catalyst UVI-6990 exhibited poor solubility in the $M_n$=1000 polypropylene glycol adduct (Example 5), and polybutylene glycol adduct (Example 9). Therefore, the formulation utilized for evaluating these epoxides was as follows:

| Component | Wt. % |
|---|---|
| Cycloaliphatic Epoxide | 42.75 |
| UVR-6110 | 42.75 |
| TONE ® 0305 | 10.0 |
| UVI-6990 | 4.0 |
| DC-57 | 0.5 |

TABLE 4

Wedge Bend for UVR 6110 TONE 0305 Formulations

| Epoxide | Avg. Wedge Bend, mm (2 trials) | Avg. Retort Wedge Bend, mm, (2 trials) | Wedge Bend, Ratio |
|---|---|---|---|
| 6128 | 21 | 56 | 2.7 |
| 6110 | 53 | 57 | 1.1 |
| Ex. 5 | 42 | 46 | 1.1 |
| Ex. 9 | 25 | 40 | 1.6 |

The adhesion, pencil hardness, MEK resistance, and cure rate results are as follows:

TABLE 5

Hardness and Cure for UVR 6110 TONE 0305 Formulations

| Epoxide | Pencil Hardness | Aluminum Pencil Hardness | MEK Resistance (double rubs) | Surface Cure Rate, fpm[1] |
|---|---|---|---|---|
| UVR-6128 Formula | 2H | 2H | 95 | 490 |
| UVR-6110 Formula | 3H | 3H | 120 | 800+ |
| Ex. 5 (PPG 1000) | 2H | 2H | 14 | 50 |
| Ex. 9 (PBG) | 2H | 2H | 13 | 100 |

[1]42% RH

Examples 12–14

The epoxide of Example 1, the bis(3,4-epoxycyclohexanecarboxylic ester) of tripropylene glycol, is included in formulations for can-end type varnish testing as follows:

| Example: Component | 12 Wt. % | 13 Wt. % | 14 Wt. % |
|---|---|---|---|
| Epoxide of Example 1 | 65.5 | 71.5 | 41.6 |
| UVR-6110 | 10.0 | 10.0 | 29.2 |
| TONE ® 0301 | — | 10.0 | 16.7 |
| TONE ® 0305 | 19.0 | — | 5.5 |
| UVI-6990 | 5.0 | 8.0 | 6.5 |
| DC-57 | 0.5 | 0.5 | 0.5 |

The formulations are applied onto tin-free steel and can-end aluminum panels with a #2.5 wirewound drawdown bar to give approximately 0.15–0.17 mils cured film thickness. All coatings are cured with 150 mJ/cm$^2$ UV dose and are baked for 10 minutes at 400 F. to simulate can end production. Cure rate is run on aluminum coated paper with one 200 W/in Linde lamp at 35% relative humidity. Wedge bend performance is determined by measuring the crack length (mm) after wedge bending the coated steel. (see wedge bend and retort procedures described above).

The coatings of Examples 12–14 give pencil hardness at least 3B and good flexibility (wedge bend less than 30). After retort treatment, the coatings retain more of their flexibility than similar coatings prepared using UVR-6128.

Examples 15–17

The epoxides of Examples 1 and 2 are included in formulations for can-end type varnish testing as follows:

| Example: | 15 | 16 | 17 |
| Component | Wt. % | Wt. % | Wt. % |
| --- | --- | --- | --- |
| Epoxide of Example 1 | 20.0 | 70.0 | 17.3 |
| Epoxide of Example 2 | 67.7 | — | 34.7 |
| UVR-6110 | — | 18.0 | 31.3 |
| Photonol 7143 | 7.8 | 7.5 | 3.0 |
| Photonol 7158 | — | — | 8.2 |
| UVJ-6990 | 4.0 | 4.0 | 5.0 |
| Silwet L-7604 | 0.5 | 0.5 | 0.5 |

The formulations are applied onto tin-free steel and can-end aluminum panels with a #2.5 wirewound drawdown bar to give approximately 0.15–0.17 mils cured film thickness. All coatings are cured with 150 mJ/cm² UV dose and are baked for 10 minutes at 400° F. to simulate can end production. Cure rate is run on aluminum coated paper with one 200 W/in Linde lamp at 35% relative humidity. Wedge bend performance is determined by measuring the crack length (mm) after wedge bending the coated steel. (see wedge bend and retort procedures described above).

The coatings of Examples 12–14 give pencil hardness at least 2B and good flexibility (wedge bend less than 30). After retort treatment, the coatings retain more of their flexibility than similar coatings prepared using UVR-6128.

Although the invention has been described above with respect to specific aspects, those skilled in the art will recognize that other aspects are intended to be included within the scope of the claims which follow.

What is claimed is:

1. A method of enhancing the toughness of a coating on an article, said coating comprising a cured cycloaliphatic epoxide derivative, wherein the cycloaliphatic epoxide derivative is a compound having the formula:

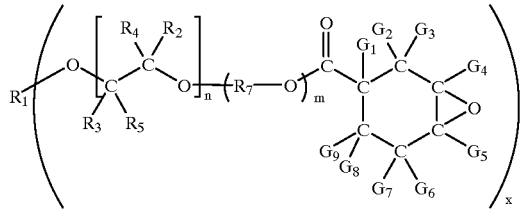

wherein $R_1$ and $R_7$ are any organic moieties capable of bonding with oxygen, $R_2$, $R_3$, $R_4$ and $R_5$ are the same or different and are hydrogen, phenyl, alkyl or alkene groups having from 1 to about 10 carbon atoms, provided that at least one of $R_2$, $R_3$, $R_4$ or $R_5$ is not hydrogen; $G_1$ to $G_9$ are the same or different and are hydrogen, phenyl or alkyl or alkene groups having from 1 to about 10 carbon atoms, n has a value of from 1 to about 30, m has a value of from 0 to about 30, and x has a value of from 1 to about 30 wherein said coating has a Wedge Bend Value before retort treatment of less than about 35 millimeters and a Wedge Bend Ratio of less than about 2.0.

2. The method of claim 1 wherein the cycloaliphatic epoxide derivative comprises the reaction product of from 40 to 95 weight percent of a cycloaliphatic epoxide carboxylic acid ester and from 5 to 60 weight percent of a hydroxy functional compound selected from the group consisting of propylene glycol, dipropylene glycol, tripropylene glycol, polypropylene glycol, bisphenol-A propoxylate, propoxylated trimethylolpropane, propoxylated glycerol, 1,2-butylene glycol, poly(1,2-butylene glycol), and poly(1,2-butylene oxide).

3. The method of claim 1 wherein m is zero.

4. The method of claim 1 wherein $R_1$ is hydrogen.

5. The method of claim 1 wherein $R_1$ and $R_7$ are each residues of a hydroxy functional compound selected from the group consisting of alcohols, glycols, polyols, hydroxy-functional acrylic polymers and copolymers, hydroxy-functional polysaccharides, hydroxy-functional polyester resins, hydroxy-functional epoxy resins and mixtures thereof.

6. The method of claim 5 wherein $R_1$ has from 1 to about 50 carbon atoms per molecule and $R_7$ has from 1 to about 20 carbon atoms per molecule.

7. The method of claim 3 wherein $R_1$ has from 1 to about 50 carbon atoms per molecule.

8. The method of claim 1 wherein one of $R_2$, $R_3$, $R_4$ or $R_5$ is methyl and the remainder are hydrogen.

9. The method of claim 1 wherein $G_1$ to $G_9$ are methyl groups or hydrogen.

10. The method of claim 1 wherein $G_1$ to $G_9$ are hydrogen.

11. The method of claim 3 wherein the cycloaliphatic epoxide derivative is selected from the group consisting of: the mono(3,4-epoxycyclohexanecarboxylic ester) of tripropylene glycol; the bis(3,4-epoxycyclohexanecarboxylic ester) of propylene glycol; the mono(3,4-epoxycyclohexanecarboxylic ester) of dipropylene glycol; the bis(3,4-epoxycyclohexanecarboxylic ester) of dipropylene glycol; the mono(3,4-epoxycyclohexanecarboxylic ester) of tripropylene glycol; the bis(3,4-epoxycyclohexanecarboxylic ester) of tripropylene glycol; the mono(3,4-epoxycyclohexanecarboxylic ester) of polypropylene glycol; the bis(3,4-epoxycyclohexanecarboxylic ester) of polypropylene glycol; the mono(3,4-epoxycyclohexanecarboxylic ester) of poly(1,2-butylene glycol); the bis(3,4-epoxycyclohexanecarboxylic ester) of poly(1,2-butylene glycol); the mono(3,4-epoxycyclohexanecarboxylic ester) of propoxylated Bisphenol-A; the bis(3,4-epoxycyclohexanecarboxylic ester) of propoxylated Bisphenol-A; the mono(3,4-epoxycyclohexanecarboxylic ester) of propoxylated trimethylolpropane; the bis(3,4-epoxycyclohexanecarboxylic ester) of propoxylated trimethylolpropane; the tris(3,4-epoxycyclohexanecarboxylic ester) of propoxylated trimethylolpropane; the mono(3,4-epoxycyclohexanecarboxylic ester) of propoxylated glycerol; the bis(3,4-epoxycyclohexanecarboxylic ester) of propoxylated glycerol; the tris(3,4-epoxycyclohexanecarboxylic ester) of propoxylated glycerol and mixtures thereof.

* * * * *